(12) United States Patent
Casper et al.

(10) Patent No.: US 6,357,442 B1
(45) Date of Patent: Mar. 19, 2002

(54) INHALATION ACTUATED DEVICE FOR USE WITH METERED DOSE INHALERS (MDIS)

(75) Inventors: Robert A. Casper, Raleigh; Frank A. Leith; David L. Gardner, both of Chapel Hill; John Medlin Snow; Zachary Wood Lyon, both of Raleigh, all of NC (US)

(73) Assignee: Innovative Devices, LLC, Raleigh, NC (US)

(*) Notice: Subject to any disclaimer, the term of this patent is extended or adjusted under 35 U.S.C. 154(b) by 0 days.

(21) Appl. No.: 09/181,150

(22) Filed: Oct. 27, 1998

Related U.S. Application Data

(63) Continuation-in-part of application No. 08/659,723, filed on Jun. 6, 1996, now Pat. No. 5,826,571.
(60) Provisional application No. 60/000,086, filed on Jun. 8, 1995.

(51) Int. Cl.[7] ............................................. A61M 11/00
(52) U.S. Cl. ......................... 128/700.23; 128/200.14; 128/203.12; 128/203.15; 128/203.23
(58) Field of Search ..................... 128/200.14–200.23, 128/200.24, 203.12, 203.15, 203.23

(56) References Cited

U.S. PATENT DOCUMENTS

| | | | |
|---|---|---|---|
| 3,565,070 A | * | 2/1971 | Hanson et al. ......... 128/200.23 |
| 3,598,294 A | * | 8/1971 | Hedrick et al. ......... 128/200.23 |
| 3,636,949 A | * | 1/1972 | Kropp ................... 128/200.23 |
| 3,789,843 A | * | 2/1974 | Armstrong et al. ..... 128/200.23 |
| 3,900,138 A | | 8/1975 | Phillips |
| 4,294,407 A | | 10/1981 | Reichl et al. |
| 4,300,456 A | | 11/1981 | Messersmith |
| 4,334,531 A | | 6/1982 | Reichl et al. |
| 4,817,822 A | | 4/1989 | Rand et al. |
| 4,877,989 A | | 10/1989 | Drews et al. |
| 5,033,463 A | | 7/1991 | Cocozza |
| 5,069,204 A | | 12/1991 | Smith et al. |
| 5,069,701 A | | 12/1991 | Pastor et al. |
| 5,119,806 A | | 6/1992 | Palson et al. |
| 5,217,004 A | | 6/1993 | Blasnik et al. |
| 5,347,998 A | * | 9/1994 | Hodson et al. ......... 128/200.23 |
| 5,349,945 A | | 9/1994 | Wass et al. |
| 5,408,994 A | | 4/1995 | Wass et al. |
| 5,427,089 A | | 6/1995 | Kraemer |
| 5,447,150 A | | 9/1995 | Bacon |
| 5,452,711 A | | 9/1995 | Gault |
| 5,482,030 A | | 1/1996 | Klein |
| 5,497,764 A | | 3/1996 | Ritson et al. |
| 5,497,765 A | | 3/1996 | Praud et al. |
| 5,564,414 A | | 10/1996 | Walker et al. |
| 5,826,571 A | | 10/1998 | Casper et al. |
| 5,904,139 A | * | 5/1999 | Hauser .................. 128/200.14 |

FOREIGN PATENT DOCUMENTS

| | | |
|---|---|---|
| EP | 0 028 929 A2 | 11/1980 |
| EP | 0 186 280 A2 | 10/1985 |
| WO | WO 97/20589 | 6/1997 |

* cited by examiner

Primary Examiner—Glenn K. Dawson
(74) Attorney, Agent, or Firm—Morriss, Bateman, O'Bryant & Compagni, P.C.

(57) ABSTRACT

A device for use with metered dose inhalers includes a housing configured with a void to receive a metered dose inhaler, an actuator assembly which is configured to selectively apply force to the metered dose inhaler to cause the metered dose inhaler to release medicament, and a cocking mechanism for placing the actuator assembly in an armed configuration. The device is configured to actuate the metered dose inhaler as the user inhales, thereby ensuring improved medicament delivery. Additionally, the device is configured to prevent the metered dose inhaler from remaining in a vented position.

22 Claims, 13 Drawing Sheets

INHALATION ACTUATED DEVICE FOR USE WITH METERED DOSE INHALERS (MDIS)

RELATED APPLICATIONS

This application is a continuation-in-part application of U.S. patent application Ser. No. 08/659,723, filed Jun. 6, 1996, now U.S. Pat. No. 5,826,571, (which is expressly incorporated herein) and which claimed the benefit of U.S. Provisional Application Serial No. 60/000,086, filed Jun. 8, 1995.

BACKGROUND OF THE INVENTION

1. Field of the Invention

The present invention relates to inhalation/breath actuated devices for use with metered dose inhalers (MDIs). Metered dose inhalers, as used herein and as commonly used in the art, are comprised of an aerosol canister which contains medicament for administration to the lungs, a metering valve which is disposed in the canister and which releases a predetermined amount of medicament from the canister when the canister is actuated, an actuator which holds the canister and includes a-opening for oral inhalation, and an actuator stem which channels the medicament released by the metering valve out through the opening and toward the user. More particularly, the present invention relates to a device which receives a metered dose inhaler and which automatically actuates the metered dose inhaler responsive to inhalation by the user.

2. State of the Art

When an asthmatic or other person suffering from inhalation problems has difficulty breathing, it is typically desirable to introduce medicament into the person's lungs to restore normal breathing patterns to the extent possible. For many years, this has been accomplished by the use of metered dose inhalers. The metered dose inhalers include a canister which contains medicament and a propellant, a metering valve which dispenses the medicament from the canister, an actuator body that receives the canister and which forms an opening for oral inhalation, and an actuator stem which receives medicament from the canister and directs it out the opening in the actuator body. Moving the medicament canister relative to the actuator body and actuator stem causes the metering valve to release the predetermined amount of medicament. Each metered dose inhalator is regulated by the U.S. Food and Drug Administration and each of the components is specifically designed relative to the parameters of the other components.

When the user is having difficulty breathing, the opening of the actuator body is placed in the user's mouth and then the canister is moved downwardly in the actuator so that the metering valve discharges the predetermined dose of medicament and propellant. The medicament passes through the actuator stem and then out the opening in the actuator body.

One problem which is recurrent in the use of metered dose inhalers is that the user often actuates the metered dose inhaler and then begins inhalation. Such an inhalation/medicating pattern limits the amount of medicament delivered to the lung and causes most of the medicament to impact the mouth and throat. Thus, the user obtains much less than an optimal dose of medicament.

In attempts to overcome the problems associated with manual actuation of the metered dose inhalers, several inhalation/breath actuated metered dose inhalers have been developed. Such devices are designed to provide proper coordination of dispensing a dose of medicament with the inhalation of the user, thus providing for the maximum proportion of the dose of medicament to be deposited in the lungs. Examples of such devices are described in U.S. Pat. Nos. 5,404,871; 5,347,998; 5,284,133; 5,217,004; 5,119,806; 5,060,643; 4,664,107; 4,648,393; 3,789,843; 3,732,864; 3,636,949; 3,598,294; 3,565,070; 3,456,646; 3,456,645; 3,456,644; British Patent Specification Nos. 2,061,116; 1,392,192; 1,335,378; 1,269,554 and German Patent No. 3,040,641.

Existing breath-actuated inhalers are designed to accommodate available aerosol canisters separate from the receiving bodies or housings for which they were originally designed, marketed, and approved by the Food and Drug Administration (FDA). Aerosol medications of the pressurized inhaler type are drug products approved and regulated by the FDA as the combination of the pressurized aerosol canister and the actuator used to atomize the canister metering valve contents. The actuator is regarded as an integral part of the aerosol drug delivery system, since the design of the housing greatly influences the nature of the aerosol spray generated for inhalation by the patient. The design of the actuator impacts not only the amount of medication released from the inhaler, but the amount of medication received by the patient due to the actuator's influence on the particle size and velocity distribution of the emitted aerosol mist and the influence of the particle or droplet size distribution and velocity on impaction in the patient's respiratory tract.

As a consequence, existing breath-actuated inhalers must be approved by the FDA in conjunction with a particular aerosol-based medication canister. As a result, these inhalers have not been generally available to the patient public for use with the full range of aerosol-based medications which are available for the treatment and management of disease. For example, a person must obtain a breath actuated device that has been approved by the FDA with the canister of medication recommended by the physician or the individual must obtain a metered dose inhaler of the desired medication, i.e., the combination of the medicament container and the actuator approved by the FDA.

A problem with many of the mechanical breath-activated inhalers is that the aerosol canister remains in the depressed position (after firing by the inhaler's internal actuation mechanism) until the patient physically intervenes and relieves the mechanical load on the aerosol canister by moving a lever, strap, or some other mechanical means. Immediately after venting, the metering chamber (valve) of the aerosol canister becomes vulnerable to the intrusion of air and the extent of air intrusion increases with the length of time the canister remains in the depressed position. The intrusion of air in this fashion can result in "vapor locking" of the metering valve, resulting in incomplete filling of the metering chamber of the valve when the canister is ultimately released from the depressed position. Incomplete filling of the metering chamber, in turn, results in incomplete dosing on the next actuation of the inhaler, due to the lower quantity of drug which has entered the metering chamber from the liquid contents of the canister.

Another problem associated with some mechanical breath-actuated inhalers is that the aerosol canister actuation mechanism must be in the "armed", ready to fire, position in order to allow recovery of the aerosol canister from the depressed position under the action of it's own internal valve spring. Two potential consequences may result from this condition. First, the actuation mechanism may be "armed" during the intervals between inhaler use or, second and of potentially more seriousness, the actuator mechanism may be "armed" during storage. This is particularly concerning when the device, as a consequence of its sale in combination with an aerosol canister as mandated by the FDA, is packaged with an aerosol canister in place. Thus, the actuator mechanism could be in the armed position for up to three years. In either event, the functional life and reliability of the device may be compromised by the long term stress effects of maintaining the actuation mechanism in the "armed" position for extended periods.

In addition to the above, the actuator mechanism may "relax" or creep, in either a fluid or bulk mechanical sense, if the device is stored for prolonged periods in the "armed" position, resulting in a change in actuator functionality with effects that may range from "premature" firing of the aerosol canister to delayed or extended firing time during the canister depression phase. In both cases the patient does not receive the prescribed dose of medication which the inhaler was designed to deliver.

Electro-mechanical inhalers are also known. U.S. Pat. No. 5,347,998 describes a breath-actuated inhaler with an electromechanical priming mechanism. It is the object of the invention described therein to provide an inhalation device for use with pressurized aerosol canisters which does not require manual priming for firing the valve contained within the aerosol canister. Further, the inhaler provides an electromechanical means for relieving the firing load imposed on the aerosol canister during actuation.

U.S. Pat. No. 5,284,133 describes a dose timer, actuator mechanism, and patient compliance monitoring means. The invention relates to a dose or timing controlled actuator that operates in conjunction with an inhalation device to prevent both patient under-compliance with prescribed medication dosing and patient abuse of or dependence on prescribed medication. The invention contemplates the use of an actuator to prevent patient actuation of the inhalation device at non-prescribed intervals or at higher than prescribed doses, and the use of an alarm to notify the patient regarding undercompliance/underdosing situations and attempted abuse situations.

U.S. Pat. No. 5,404,871 describes an apparatus and method for delivering an amount of aerosolized medicine for inspiration by a patient in response to the occurrence of an appropriate delivery point or points in the patient's detected breath flow. Changes in a patient's breath flow pattern during the course of an aerosolized medication inspiration therapy program may be detected and used to adjust the controlled amount of medication to be delivered in a given administration and/or to conform to the pattern of the patient's condition or change in condition. The device may also contain a library of administration protocols or operating parameters for different medications and means for identifying, from the canister, the medicinal contents of the canister for customizing operation of the apparatus.

U.S. Pat. No. 5,497,764 describes a portable, battery powered, hand-held system for releasing a controlled dose of aerosol medication for inhalation by a patient including a durable body and an aerosol medication cassette inserted in the durable body. The durable body includes an actuator mechanism for engaging an inserted cassette and its canister, and an actuator release mechanism for controlling the actuator mechanism to depress the canister for a selected period of time to release the desired dose of medication and then release the canister. The actuator mechanism, includes a compression spring for depressing the canister and a torsion spring for reloading the compression spring. The torsion spring is reloaded by rotating the cassette from an open position for delivering aerosol to a closed position. The actuator release mechanism includes a motor and trigger in assembly that controls the release of the compression spring and the torsion spring, and, hence, the time that the canister is depressed.

An additional problem with the presently available breath/inhalation actuated metered dose inhalers is the risk which is posed by actuator failure. Because the devices replace the conventional actuator body, many of them have no mechanism which permits manual actuation of the canister in the event the breath/inhalation activated mechanism fails. If a spring or other component of the devices were to fail, the user may have no way to dispense the medicament contained within the canister. Thus, a user may be deprived of medicament while undergoing an asthma attack due to actuator failure.

Thus there is a need for an improved device for use with metered dose inhalers. Such a device should be easy to use and relatively inexpensive. Additionally, such a device should not require replacement if new medication is to be used, and should allow for conventional actuation of the metered dose inhaler when desired.

OBJECTS AND SUMMARY OF THE INVENTION

It is therefore an object of the present invention to provide a novel inhalation device for use with metered dose inhalers (MDIs).

It is another object of the present invention to provide a device for use with metered dose inhalers which dose not require replacement of the device when medicament is changed.

It is another object of the present invention to provide an inhalation device for use with metered dose inhalers which includes a mechanical mechanism for applying the force required to actuate a metered dose inhaler at a preset patient inspiration flow rate.

It is still another object of the invention to provide such a device wherein the metered dose inhaler is physically incorporated into the device with the aerosol canister still housed in the actuator for which the medication has received FDA approval.

It is yet another object of the present invention to provide an auto-return mechanism for returning the aerosol canister of a metered dose inhaler to a "resting" position within a brief time following actuation to assure that the metered dose inhaler is properly "primed" for administration of a subsequent dose.

It is a further object of the present invention to provide viscoelastic means for controlling the timing function of the auto-return mechanism.

It is yet a further object of the present invention to provide means for arming the mechanical metered dose inhaler actuation mechanism, just prior to use, by incorporating the arming function with opening of the device for use.

It is still a further object of the present invention to provide a mechanical override mechanism by which the metered dose inhaler may be actuated by the mechanical actuation mechanism without the necessity of the patient achieving the predetermined inspiration flow rate.

It is still a further object of the present invention to provide a dose-counting means associated with the metered dose inhaler actuation to count the number of medicament doses dispensed or available from the aerosol canister.

Still yet another object of the present invention is the provision of a blocking mechanism to prevent premature firing. Preferably, such a mechanism would prevent firing when the mouthpiece is closed and the manual actuation button depressed, or by accidental droppage of the unit with the mouthpiece closed.

Still another object of the present invention is to provide an adaption mechanism to facilitate use of different sizes and styles of FDA approved metered dose inhalers (aerosol canisters and the associated actuator).

The above and other objects of the invention not specifically recited are realized in specific illustrated embodiments of a breath/inhalation actuated device for use with metered dose inhalers including a housing having a cavity formed therein which is configured for receiving the aerosol canister and the actuator body of a metered dose inhaler and holding the metered dose inhaler in communication with an opening in the housing for dispensing medicament therethrough from the metered dose inhaler. The device also includes a mechanism for automatically activating the metered dose inhaler in response to inhalation of a user through the opening to vent the aerosol canister and provide medicament to the user.

In accordance with one aspect of the invention, the device also includes a return mechanism for automatically deactivating a vented metered dose inhaler to its unvented position where medicament is no longer dispensed therefrom. Preferably, the return mechanism acts in response to the activating means.

In accordance with another aspect of the invention, the housing comprises a cap covering the opening when the cap is in a closed position and exposing the opening when the cap is in an open position. The cap is moveable from its closed position to its opened position in such a manner as to arm the means for depressing the metered dose inhaler.

In accordance with yet another aspect of the present invention, the device further includes a control mechanism for controlling the time of venting of a metered dose inhaler. In a preferred embodiment, the control mechanism includes a mechanism which returns the aerosol canister to the unvented position, and a deformable viscoelastic element which creates a delay for increasing the amount of time the aerosol canister is in the unvented position.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
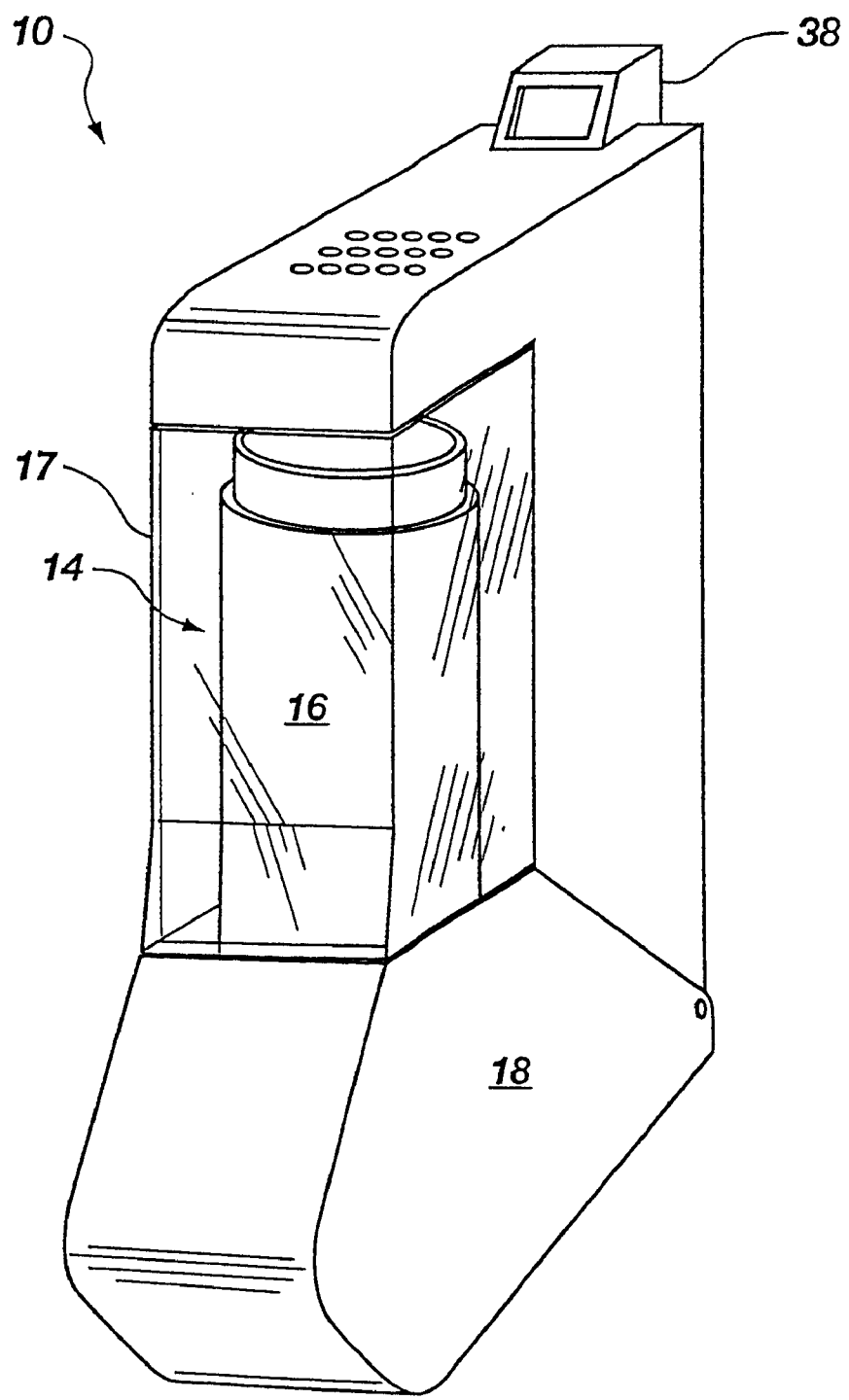
FIG. 1 is a perspective view of a breath/inhalation actuated device for use with metered dose inhalers in accordance with the principles of the present invention.
Figure 2:
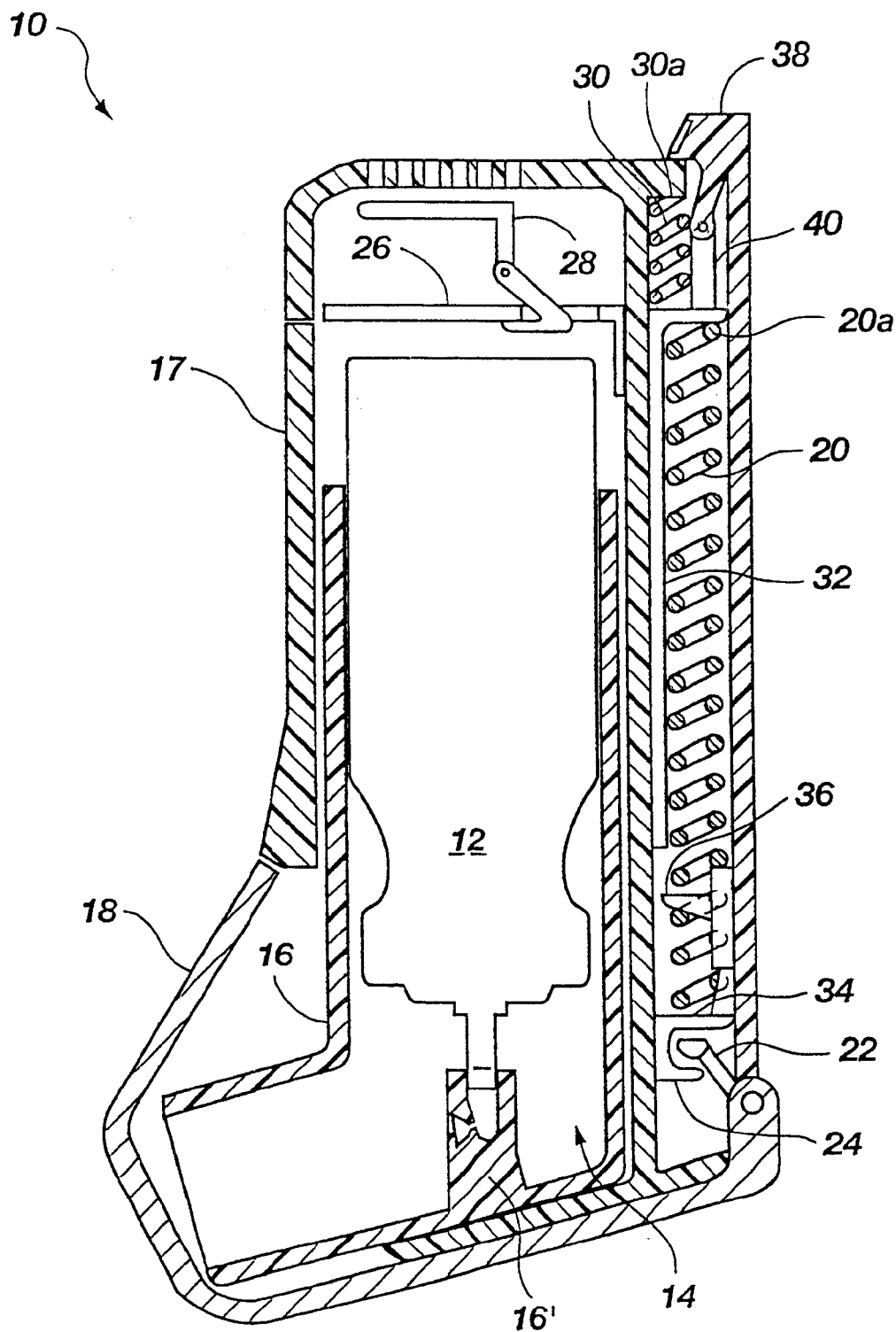
FIG. 2 is a vertical cross-sectional view of the breath/inhalation actuated device shown in FIG. 1.

Referring to FIGS. 1 and 2, the present invention provides an inhalation actuated device, generally designated 10, for mechanically actuating an aerosol canister 12 of a metered dose inhaler, generally designated 14, under the action of a patient's inspiratory flow. As such, the inhalation actuated device 10 alleviates the difficulty most patients experience in coordinating inhalation and manually actuating the metered dose inhaler to achieve optimal deposition of medication in the lungs. Additionally, the inhalation actuated device also restores the aerosol canister 12 to a "resting" position, thereby preventing the aerosol container from being held in a vented position for a prolonged period of time.

The metered dose inhaler 14, consists of the medicament-containing aerosol canister 12, and an associated actuator body 16 with a actuator stem 16' disposed therein for receiving the aerosol canister 12. The entire metered dose inhaler 14 is incorporated directly into the inhalation device 10 by the patient. Thus, the inhalation device 10 may be used with a variety of different metered dose inhalers without concern that the inhalation device will affect the medicament dose which the metered dose inhaler provides.

The relationship between the metered dose inhaler 14 and the inhalation actuated device 10 can be seen in FIGS. 1 and 2. Inhalation actuated device 10 typically includes an access panel 17 which can be used to open the inhalation activated device 10 to enable placement and removal of the metered dose inhaler 14 from the device. Access panel 17 can be transparent in order to be able to see MDI 14 therethrough, but it is envisioned according to this invention that access panel 17 could be opaque as well.

"Arming" T of the mechanical actuating mechanism of this invention may be initiated by a user by opening a mouthpiece cover or protective dust cap 18 which is operatively connected to power spring 20 by a latching mechanism. As shown in FIG. 2, the latching mechanism can comprise arm 22 and receiving member 24 for operatively receiving arm 22 and which is connected to power spring 20. Opening dust cap 18 latches and stretches power spring 20. The distal end 20a of the dust cap 18 is connected to an actuating platform 26 which is latched in the fixed position by a breath or inspiration-actuated catch/release mechanism 28. Actuating platform 26 is further connected to a weaker return spring 30, the distal end 30a of which is affixed to the housing of device 10.

When a user inhales and reaches a predetermined inspiration flow rate, breath-actuated catch/release mechanism 28 releases actuating platform 26 and the force stored in "stretched" power spring 20 pulls the actuating platform 26 downward. The actuating platform 26 depresses and vents the aerosol canister 12 housed in device 10 and releases medicament contained therein as an aerosol mist. Importantly, as the aerosol canister 12 is depressed, it engages the actuator stem 16' to cause the release of the medicament. Thus, the metered dose of medicament is the same as if the metered dose inhaler 14 were used manually by the user. In other words, the medicament delivered to the patient is in the same quantities, etc. as that for which the metered dose inhaler was approved by the Food and Drug administration.

Immediately or shortly after the metered dose inhaler 14 is actuated, receiving member 24 of the latching mechanism is released from its latched position with arm 22 by the action (contact) of rod 32, which is functionally attached to actuating platform 26. Release of the receiving member 24 allows the actuating platform 26, the power spring 20 and the lower platform 34 to move upwardly under the retractive action of return spring 30.

As actuating platform 26 proximally approaches its "resting" position it engages breath-actuated catch/release mechanism 28 and becomes immobilized under the action of the latching means associated therewith. The upward movement of actuating platform 26 under the action of return spring 30 allows aerosol canister 12 to move upward under the action of its internal metering valve spring (not shown) to its "resting" position. During the course of the canister's movement upward, the metering chamber of aerosol canister 12 refills with fluid contents from the canister volume.

This auto-return feature of the present invention is an advance over other mechanical inhalers for which a user must intervene to return the aerosol canister to its resting position, either by "rearming" the device or by some other mechanism. In this case, there is no control over the period of time during which the aerosol canister remains in the depressed (vented) position. In the vented position a canister metering valve is subject to intrusion of air from the environment. If a canister remains in the vented position for too long, "vapor" locking of the metering valve may occur when the canister is finally released from the depressed position. In the prior art devices, all or a portion of the air in the metering chamber may not be eliminated during the filling cycle and this remaining air displaces volume that would normally be filled with fluid from the canister contents. Consequently, a lower than specified dose of medicament is present in the metering chamber at the end of the filling cycle, manifested as a lower dosing of medication when the user next actuates the metered dose inhaler.

Timing control of the venting period of the aerosol canister, such as aerosol canister 12, is achieved by incorporation of a viscoelastic element which serves to slow the downward movement of the actuating platform after venting of the aerosol canister has begun. In one embodiment and as shown in FIG. 2, the viscoelastic element is incorporated as a fixture, such as viscoelastic element 36, on lower platform 34 and is acted upon by rod 32 connected to actuating platform 26. The viscoelastic element 36 may be polymeric in nature or may be constructed via a traditional spring and dashpot arrangement.

On actuation, power spring 20 provides the force for actuating the canister 12 to ensure complete venting by movement of the actuating platform 26 in a downward fashion. Rod 32 is integrated into actuating platform 26 and travels with actuating platform 26 as it moves downward. Within a short distance from its "resting", latched position, actuating platform 26 contacts aerosol canister 12 and pushes it downward under the influence of power spring 20. As canister 12 moves downward, its metering chamber moves axially with respect to the end of the valve stem until the metering chamber begins to vent its contents. Canister 12 continues its downward movement until rod 32, by means of an associated "stop", contacts the viscoelastic element 36. The point of contact with the viscoelastic element 36 preferably coincides with a point intermediate between the position at which the metering chamber vents and the point at which the aerosol canister valve spring (not shown) is fully compressed at its "bottom out" position.

Upon contacting the viscoelastic element 36, the downward motion of actuating platform 26 slows considerably, advancing downward under the influence of power spring 20 at a rate governed primarily by the time-dependent deformation of the viscoelastic material. This slowing of the downward motion of actuating platform 26 serves to provide the time required for complete venting of the metering chamber. Rod 32 continues to move slowly downward as viscoelastic element 36 deforms until rod 32 contacts lower platform 34 which can be a part of receiving member 24. At this point lower platform 34 is released from its latched and fixed position and actuating platform 26 is free to move upward under the influence of its return spring 30 and possibly even with assistance provided by the internal aerosol canister valve spring (not shown). As actuating platform 26 moves upward, lower platform 34 also moves upward under the action of the power spring 20. The aerosol canister metering chamber remains vented to the atmosphere until the upward movement of the canister results in sealing off of the stem connection between the metering chamber and the atmosphere. The process provides a means of controlling the time period during which the metering chamber is vented to the atmosphere, optimally allowing for a venting period of 300–500 milliseconds (ms), to prevent undesired air intrusion.

Actuating platform 26 is further connected to a counter 38 by a connecting rod 40 which advances counter 38 by one unit for each complete canister actuation/recovery cycle. This arrangement provides the user with an indication of the number of doses of medication used or remaining in the canister. The counter may be reset to a base value when an exhausted metered dose inhaler is replaced.

Figure 3:
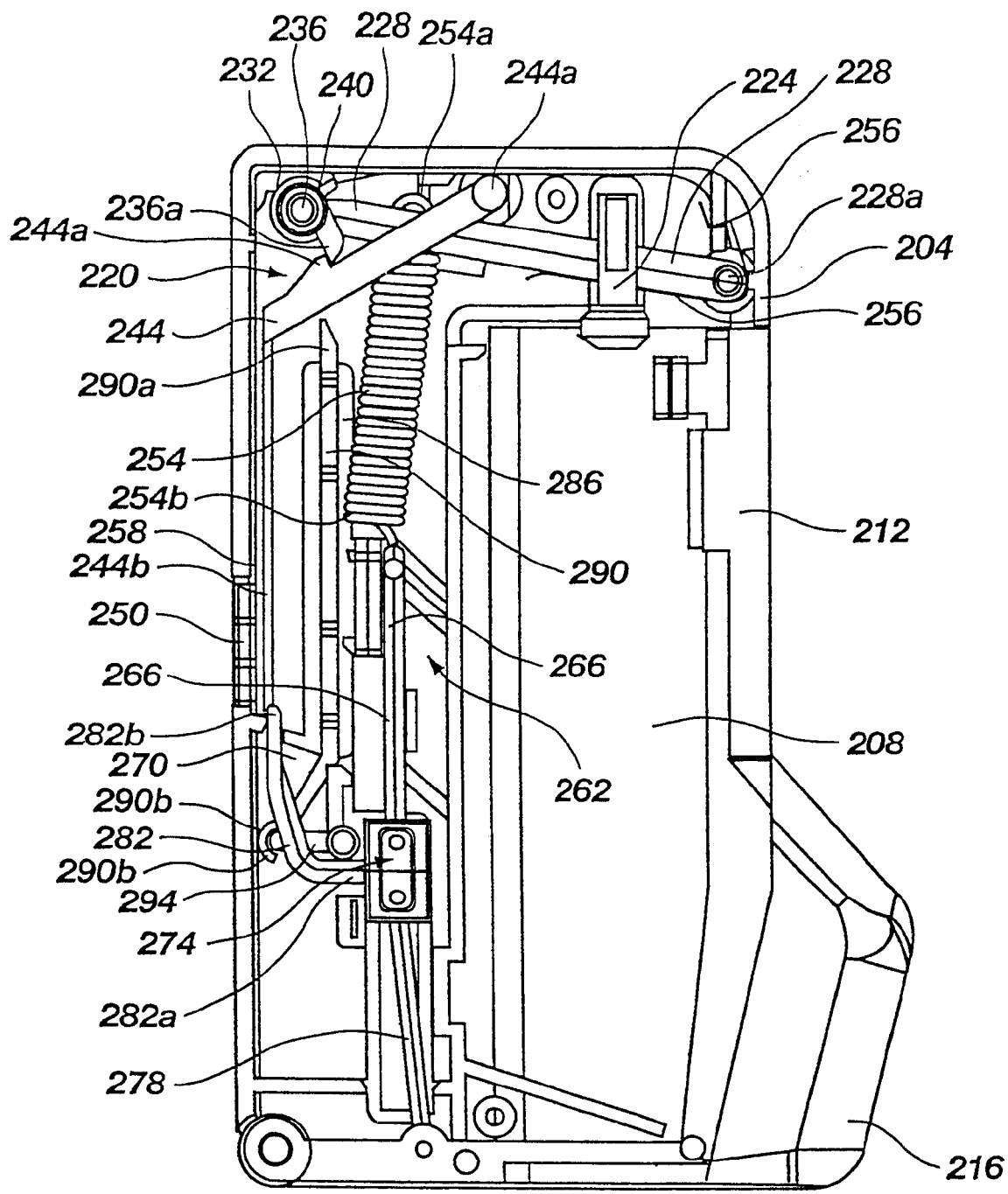
FIG. 3 shows a side view of an alternative embodiment of a device for use with metered dose inhalers in accordance with the principles of the present invention, the device being empty and in a static state wherein no load is placed on the actuation mechanism.

It will be understood that various details of the invention may be changed without departing from the scope of the invention. For example, in FIGS. 3 through 4, there is shown a preferred embodiment of an inhalation actuated device for use with a metered dose inhaler. Referring specifically to FIG. 3, there is shown a side view detailing the inner workings of an inhalation actuated device, generally indicated at 200, for use with metered dose inhalers. Beginning on the right side of FIG. 3, the inhalation actuated device 200 includes a housing body 204 which is configured with a void 208 configured to receive the aerosol canister and actuator body of a metered dose inhaler (shown in FIG. 3A).

To enable placement of the metered dose inhaler in the void 208 in the housing 204, a door 212 is pivotably attached to the housing. By rotating the door 212 approximately 180 degrees relative to the housing 204, an opening is formed, thereby providing access to the void 208. The housing 204 also includes a cover or dust cap 216. The dust cap 216 pivots with respect to the housing to expose the inhalation opening of the medicament inhalator. Pivoting of the dust cap 216 also arms the actuation mechanism, generally indicated at 220, as is described in detail below.

To move the aerosol canister of the metered dose inhaler and thereby release medicament, the actuation mechanism 220 includes a plunger 224 which is positioned at the top of the void 208 in the housing 204. The plunger 224 is disposed on a lever arm 228. A first end 228a of the lever arm 228 is pivotably attached to the housing 204 so as to allow the lever arm to rotate and move the plunger 224 generally vertically.

An opposing second end 228b of the lever arm 228 is selectively engaged by a catch mechanism 232 which is also attached to the housing 204. The catch mechanism 232 selectively engages the second end 228b of the lever arm 228 to selectively prevent pivoting of the lever arm. When the catch mechanism 232 engages the lever arm 228, the lever arm is unable to rotate, thereby preventing any meaningful movement of the plunger 224. Once the catch mechanism 232 no longer engages the lever arm 228, the lever arm is free to rotate downwardly, thereby moving the plunger 224 downwardly to actuate a metered dose inhaler disposed in the void 208.

The catch mechanism 232 includes a rotary sear 236 and an internal vane return spring 240. The rotary sear 236 rotates to engage an internal vane 244. An upper first end 244a of the internal vane 244 is pivotably attached to the housing 204. An opposing lower second end 244b is disposed adjacent a rear air intake port 250. When a user inhales through the opening in the actuator body of the metered dose inhaler, air is drawn into the housing 204 through the rear air intake port 250 causing movement of the internal vane 244, release of the catch mechanism 232 and allowing movement of the lever arm 228 as described move fully below.

In addition to the structures discussed above, the lever arm 228 is also attached to a power spring 254 adjacent its second end 228b, and a return spring 256 adjacent the lever arm's first end 228b. The power spring 254 is configured to forcefully rotate the lever arm 228 downward to thereby actuate a metered dose inhaler with the plunger 224, while the return spring 256 is configured to help return the lever arm to the position shown in FIG. 3.

The power spring 254 is attached at a first, upper end 254a to the lever arm 228. An opposing lower end 254b is attached to a spring plate 258. The spring plate 258 forms a part of a spring latch assembly, generally indicated at 262, and is configured to receive a pawl 266 and a latch 270.

The pawl 266 is attached to a link block 274, which is attached to a connector arm 278. The connector arm 278, in turn, is connected to the dust cap 216 such that rotation of the dust cap downwardly causes downward movement of the connector arm 278, the link block 274 and the pawl 266.

The spring latch assembly 262 also includes a positioning arm 282. A first end 282a of the positioning arm is attached to the link block 274. The positioning arm 282 extends rearwardly and upwardly to a second end 282b which terminates adjacent the second end 244b of the internal vane 244.

Also shown in FIG. 3 is a pair of walls 286 disposed adjacent the power spring 254. The walls 286 define a channel in which slides a knock-off mechanism 290. An upper first end 290a of the knock-off mechanism 290 is position below the lever arm 228 or some attachment thereto such that downward movement of the lever arm 228 causes downward movement of the knock-off 290. The opposing second end 290b of the knock-off 290b (which looks similar to an open ended wrench) engages a rotatable arm 294 which is connected to the latch 270.

Figure 3A:
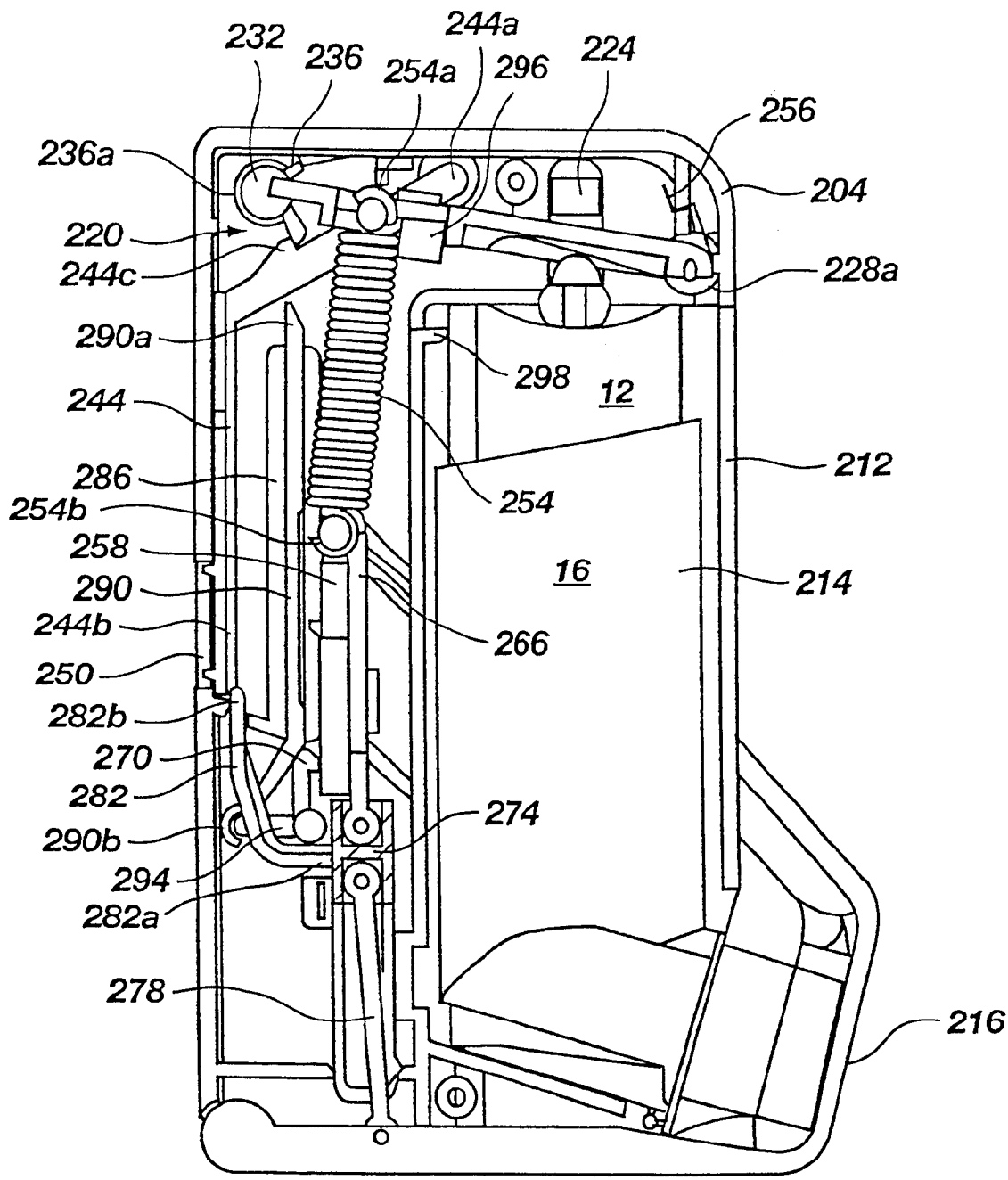
FIG. 3A shows a side view of the embodiment of FIG. 3 in the static state and with a metered dose inhaler disposed therein.

The operational cycle of the device 200 will be discussed with respect to FIGS. 3A through 3H in detail. In FIG. 3A, there is shown a view similar to that shown in FIG. 3, with the exceptions that the link bloc 274 is shown in cross-section, and the metered dose inhaler 14 (including the aerosol canister 12 and the actuator body 16) is disposed in the device 200.

As shown in FIG. 3A, device 200 is in a static state. In other words, none of the components are in a loaded position. The power spring 254 is in a retracted position because the spring plate 258 has not been pulled downwardly. The catch mechanism 232 is static because the power spring 254 is not pulling downwardly on the lever arm 228. Additionally, because the lever arm 228 is in a first, upper orientation, the return spring 256 is disposed in its resting position.

FIG. 3A also shows an enhanced view of a damp block 298. The damp block 296 is disposed on the lever arm 228 and is positioned to engage a wall 298. The damp block 296 serves as a timing control along the displacement cycle.

Figure 3B:
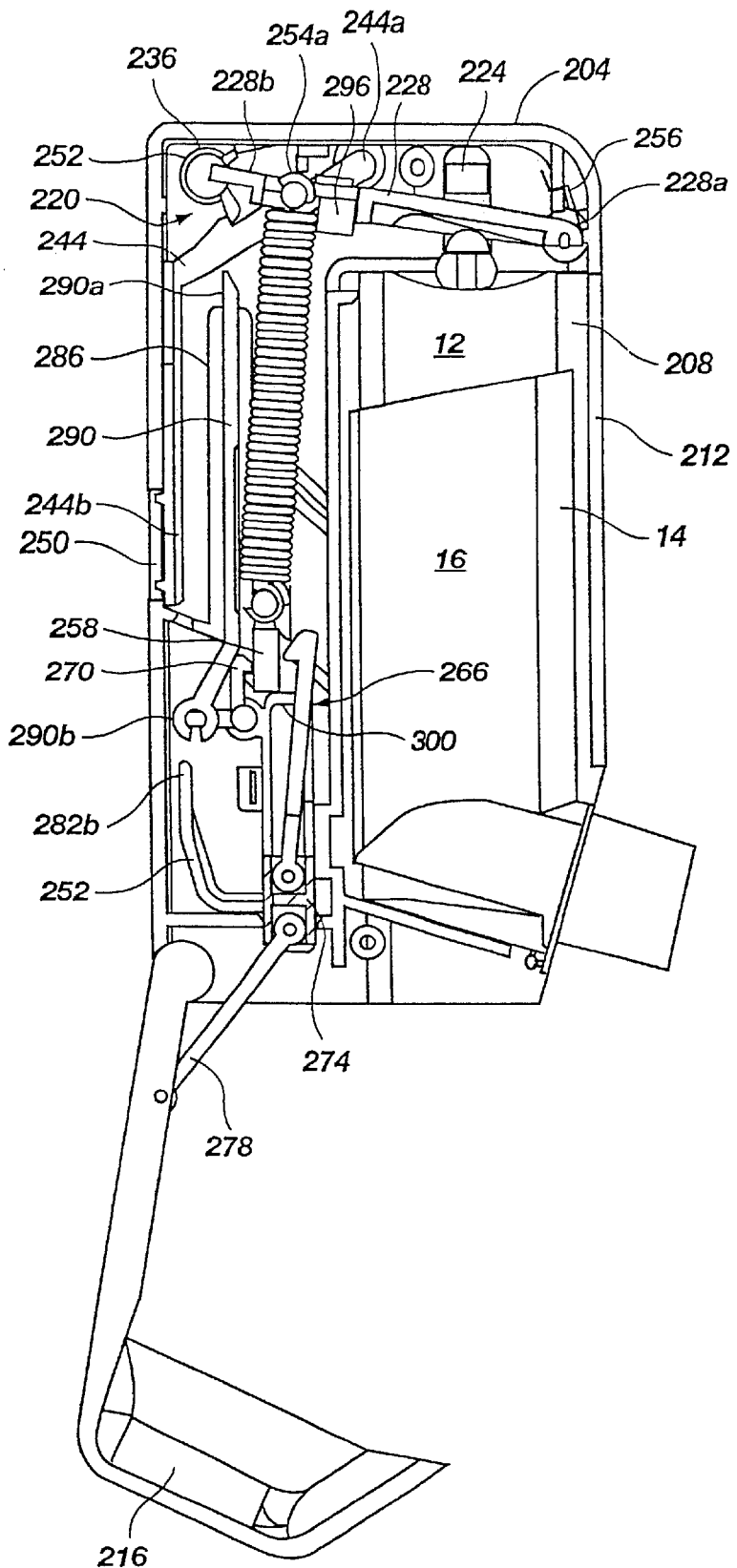
FIG. 3B shows a side view of the embodiment of FIGS. 3 and 3A with the actuation mechanism with the dust cap being used to cock the device into a loaded state preparatory to actuation.

Turning now to FIG. 3B, there is shown a side view similar to that shown in FIG. 3A, except that the dust cap 216 has been rotated approximately 105 degrees with respect to the housing 204. Rotation of the dust cap 216 causes the connector arm 278 (which is attached at a lower end to the dust cap) to move downwardly. Downward movement of the connector arm 278 causes a similar downward movement of the link block 274 to which the connector arm 278 is pivotably attached.

The link block 274 is also pivotably attached to the pawl 266. Downward movement of the link block 274 causes downward movement of the pawl 266. The pawl 266, in turn, moves the spring plate 258 downwardly, thereby loading the power spring 254.

Once the pawl 266 has carried the spring plate 258 to its bottom extreme, the pawl pivots out of engagement with the spring plate. The spring plate 258 remains in the extended position due to the latch 270 which is disposed on the opposite side of the spring plate from the pawl 266. Thus, the power spring 254 is held in a loaded or armed position.

Figure 3C:
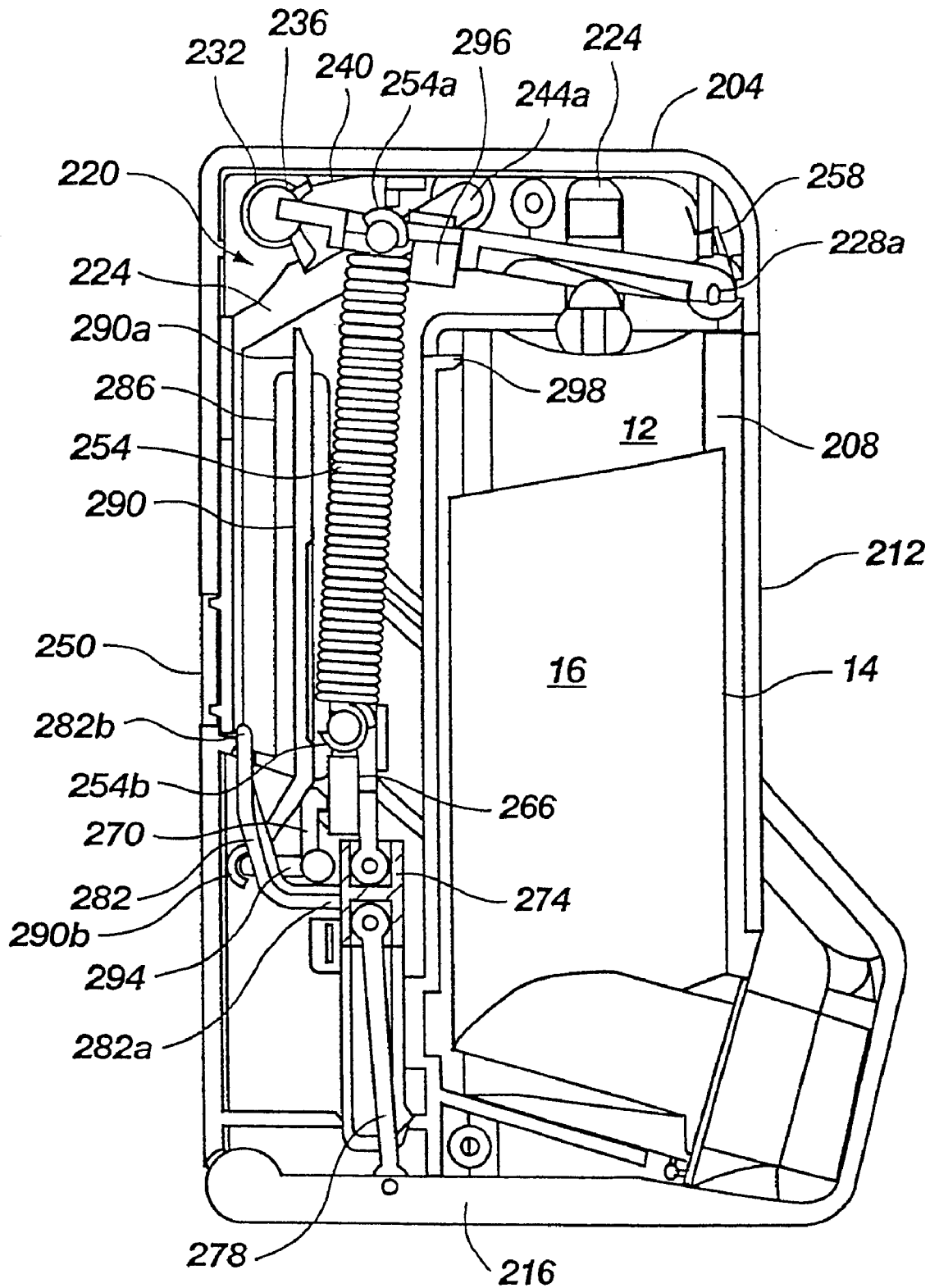
FIG. 3C shows a side view of the embodiment of FIGS. 3 through 3B with the actuation mechanism in the loaded state and the dust cap closed.

One advantage of the present invention is that the device 200 can be armed without the need for firing. Turning now to FIG. 3C, there is shown a view similar to that shown in FIG. 3B, with the exception that the dust cap 216 has been rotated back into the position shown in FIG. 3A. Closing the dust cap 216, neither disarms the actuating mechanism 220, nor causes actuation of the metered dose inhaler 14. Thus, if the user opens the dust cap 216 and then determines that medicament is not needed, the dust cap 216 may be closed. Alternatively, those users who arm fearful that they might not fully cock the dust cap 216 to arm the actuation mechanism 220 during an attack can leave the actuation mechanism in an armed orientation so that the dust cap need only be opened sufficiently to provide access to the metered dose inhaler.

The actuation mechanism 220 of the device 200 is able to remain in an armed orientation because of the ability of the pawl 266 to disengage the spring plate 258 once the spring plate is in position to be held by the latch 270. With the latch 270 holding the spring plate 258, the dust cap 216 can be opened repeatedly without causing the metered dose inhaler 14 to be actuated.

Figure 3D:
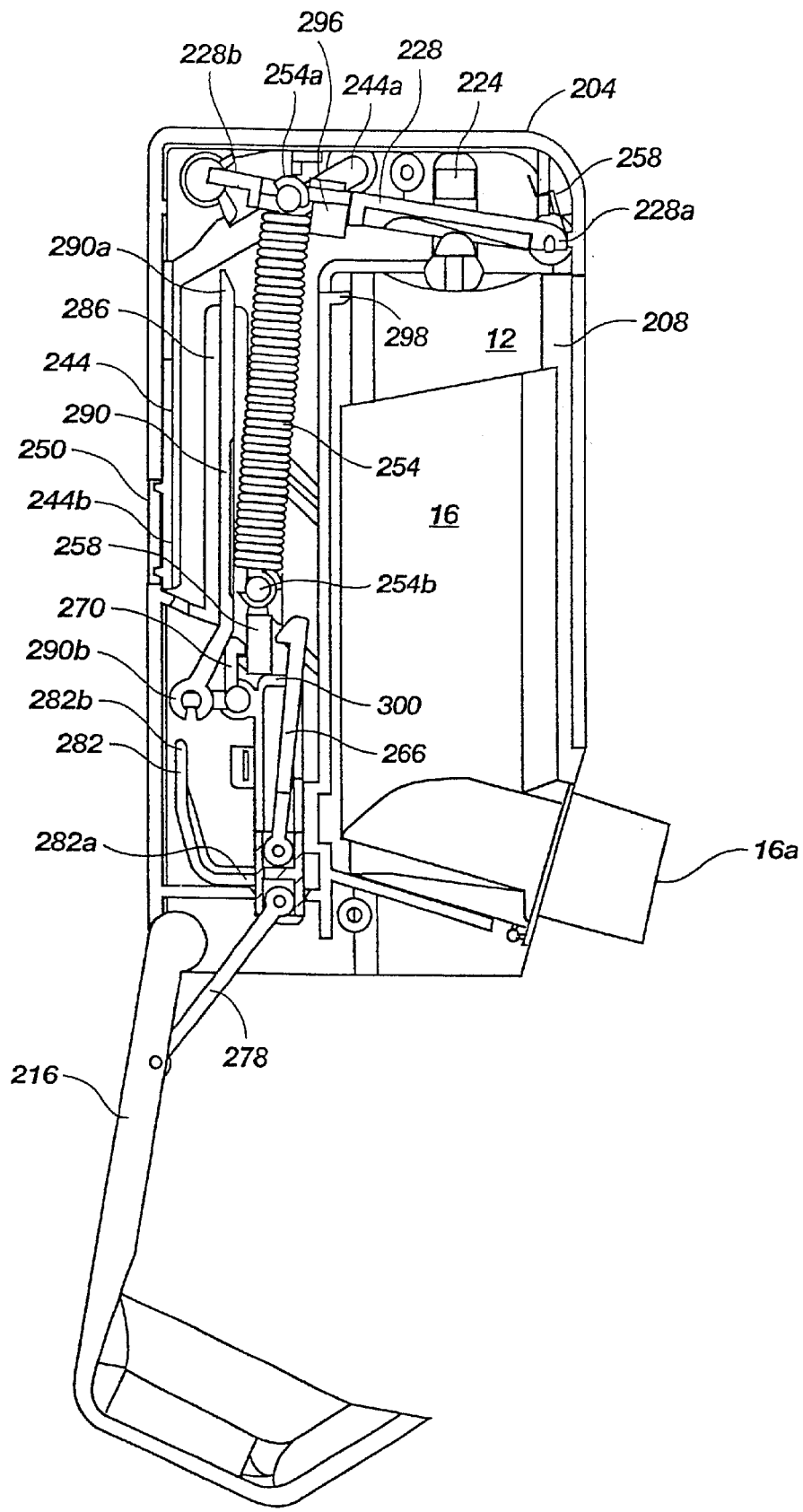
FIG. 3D shows a side view similar to that of FIG. 3B with the device ready for actuation.

FIG. 3D shows a side view of the device 200 and the metered dose inhaler 14 which is substantially the same as that shown in FIG. 3B. The dust cap 216 has been returned to the open position, wherein it is rotated away from the opening 16a of the actuator body 16 of the metered dose inhaler. The spring plate 258 remains in the armed position wherein it is held by the latch 270.

Figure 3E:
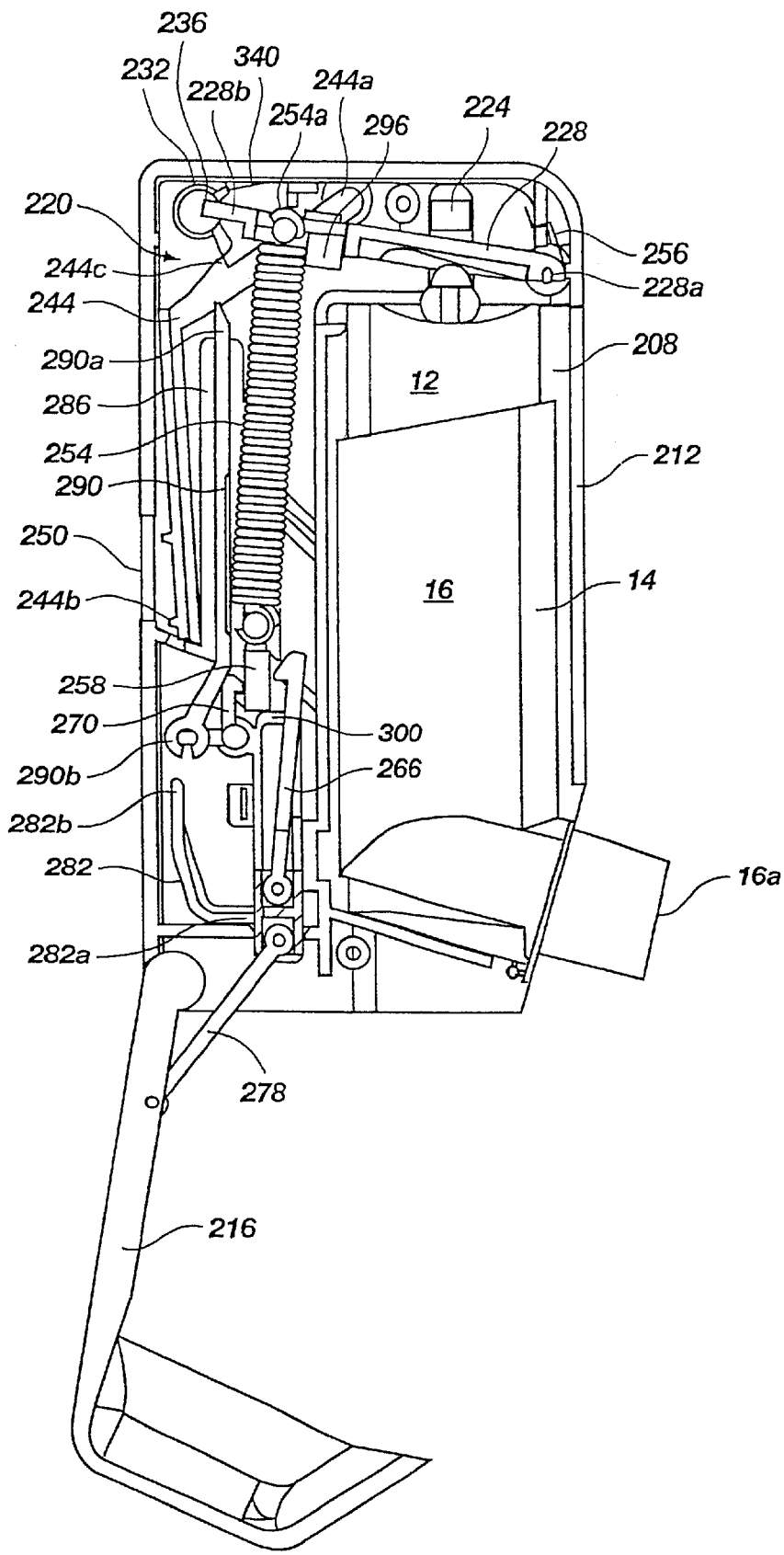
FIG. 3E shows a side view of the embodiment of FIGS. 3 through 3D at the beginning of the actuation cycle as a user inhales to move the internal vane and release the actuation mechanism.
Figure 3F:
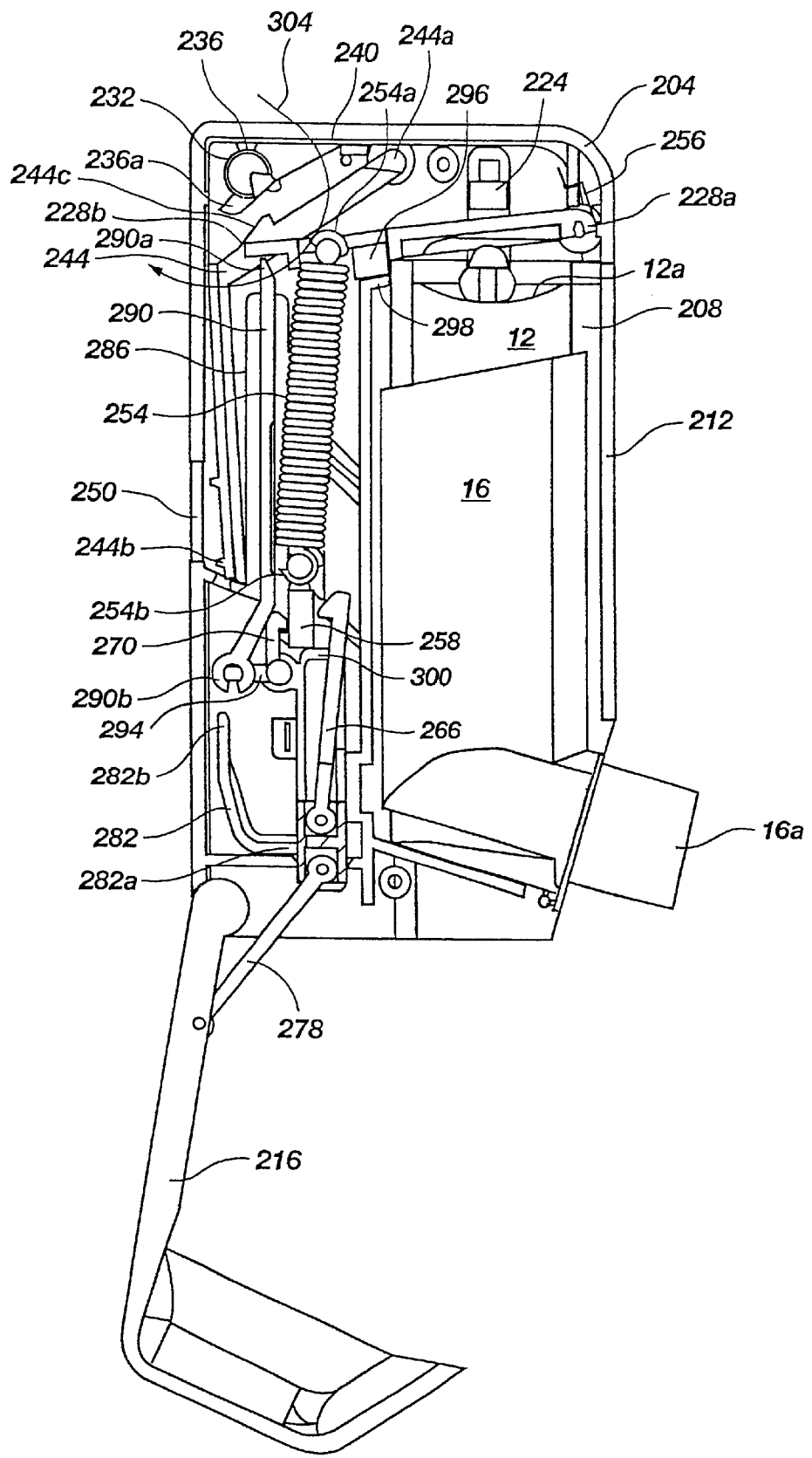
FIG. 3F shows a side view of the embodiment of FIGS. 3 through 3E at an intermediate state of the actuation cycle as the canister of the medicament inhalator is depressed to release medicament out through the actuator body.

Referring now to FIG. 3E, there is shown a side view similar to that shown in FIG. 3D, but with the actuation mechanism 220 in the beginning stages of actuating the metered dose inhaler 14. As the user-inhales through the opening 16a of the actuator body 16, a vacuum is created within the void 208. In response to the vacuum, air flows into the housing 204 through the rear air intake port 250 at the rear of the housing.

The pressure differential between the ambient air and the vacuum created the void 204 by the user's inhalation causes the second, lower end 244b of the internal vane 244 to move toward the void 208. Movement of the second, lower end 244b of the internal vane 244 causes rotation of the internal vane 244 about the first, upper end 244a. Because the internal vane 244 has a return spring 240 disposed in communication therewith, the amount of air necessary to move the internal vane 244 is more than might flow through the rear air intake port 250 due to a small breeze etc. Preferably, the resistance provided by the internal vane 244 return spring 240 is correlated to a desired inhalation rate to ensure that the user is inhaling deeply before the internal vane is rotated.

As the internal vane 244 rotates, a tab 244c on the rotatable internal vane begins to move relative to an engaging tab 236a of the rotary sear 236. As long as the tab 236a of the rotary sear 236, and the tab 244c of the internal vane 244 remain engaged, the lever arm 228 will remain in the first, upper position.

As the internal vane 244 rotates with respect to its first, upper end 244a, however, the tab 244c of the internal vane disengages the tab 236a of the rotary sear 236. Once the engagement has terminated, the rotary sear 236 is able to rotate clockwise (relative to this view orientation) in the manner indicated by arrow 304 in FIG. 3F. Rotation of the rotary sear 236, in turn, releases the second end 228b of the lever arm 228.

With the second end 228b of the lever arm 228 released from the rotary sear 236, the lever arm 228 is free to pivot about the first end 228a which is pivotably attached to the housing 204. Because the first end 254a of the power spring 254 is attached to the lever arm 228 adjacent the second end 228b, and because the spring plate 258 is holding the lower end 254b of the power spring so that the spring is under tension, the second end 228a of the lever arm rotates downwardly with a significant amount of force. The damp block 296 engaging the wall 298 provides a momentary delay in the return of the lever arm 228 to its upper position and thereby allows the aerosol canister to fully vent.

The downward rotation of the lever arm 228 also causes downward movement of the plunger 224 which is attached to the lever arm. The downward movement of the plunger 224 causes downward movement of the aerosol canister 12 with respect to the actuator body 16 of the metered dose inhaler 14. This, of course, causes the metering valve (not shown) to release medicament, which is channeled through the actuator stem (not shown) and out the opening 16a of the actuator body 16 for inhalation by the user.

Once the metered dose inhaler 14 has been actuated by the actuation mechanism 220 to release medicament, it is important that the metered dose inhaler 14 not be maintained in a vented configuration. If the aerosol canister 12 remains pressed down into the actuator body 16 for a prolonged period of time, air will work its way into the aerosol metering valve. The air can cause vapor locking and interferes with the ability of the metering valve to provide consistent doses of medicament.

To prevent such problems, the device 200 of the present invention is configured to enable the aerosol canister 12 to return to an unvented position. Additionally, the device 200 is configured to automatically return to a position in which it may be cocked and then actuated.

To ensure return of the aerosol canister 12 to an unvented position, the device 200 is configured to prevent the lever arm 228 and plunger 224 from continuing to apply pressure to the canister after the actuation mechanism 220 has been actuated. As the lever arm 228 rotates downwardly, the lever arm or some projection attached thereto impacts the upper first end 290a of the knock-off 290. The force from the lever arm 228 pushes the knock-off 290 downwardly between the walls 286. The second, lower end 290b of the knock-off 290 is moved downwardly and rotates the rotatable arm 294.

Figure 3G:
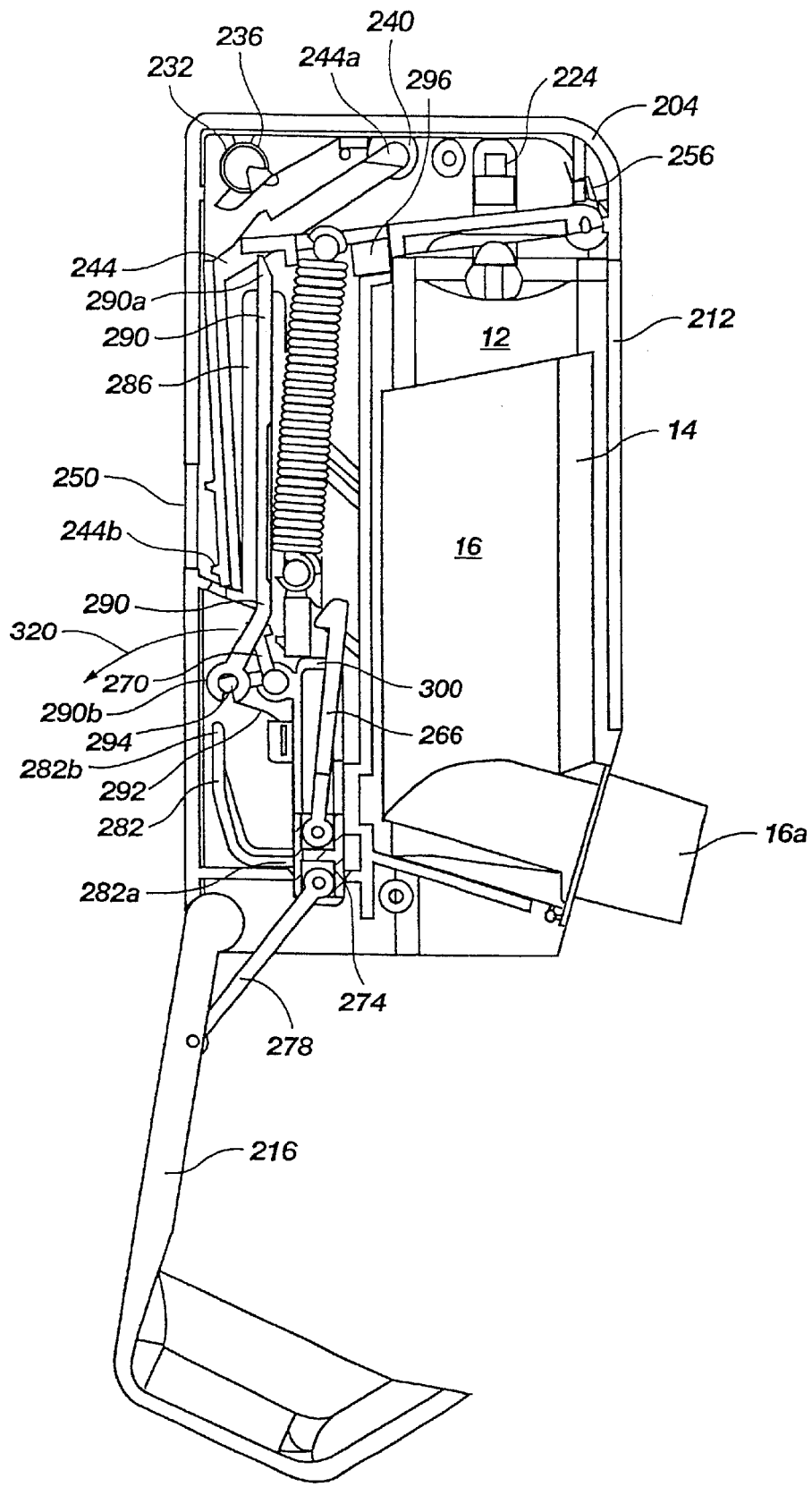
FIG. 3G shows a side view of the embodiment of FIGS. 3 through 3F at an intermediate stage immediately following that shown in FIG. 3F and wherein the knock-off is moved to release the power spring.

Because the rotatable arm 294 is attached to the latch 270 which holds the spring plate 258, downward movement of the rotatable arm causes the latch to rotate away from the spring plate 258 as shown in FIG. 3G. Once the latch 270 rotates away from the spring plate 258, the spring plate and the lower end 254b of the power spring 254 are no longer held in the lower position. The spring plate 258 is not held in place by the pawl 266 due to the wall 300. Thus, movement of the knock-off 290 serves as a release for the spring plate 258 and the power spring 254 attached thereto. With the power spring 254 no longer held at the lower end 254b, the power spring no longer applies a strong downward force on the lever arm 228.

FIG. 3G shows the position of the actuation mechanism 220 at the latter stages of the inhalation cycle. The internal vane 244 remains in a rotated open position where the lower end 244b is rotated away from the rear air intake port. The lever arm 228 is in the second, lower position 228 in which the plunger 224 continues to hold the aerosol canister 12 in a vented state. Additionally, the knock-off 290 has been moved into the lower position wherein the lower end 290b of the knock-off 290 rotates the rotatable arm 294 and removes the latch 270 from the spring plate 258 as indicated by the arrow 320.

Figure 3H:
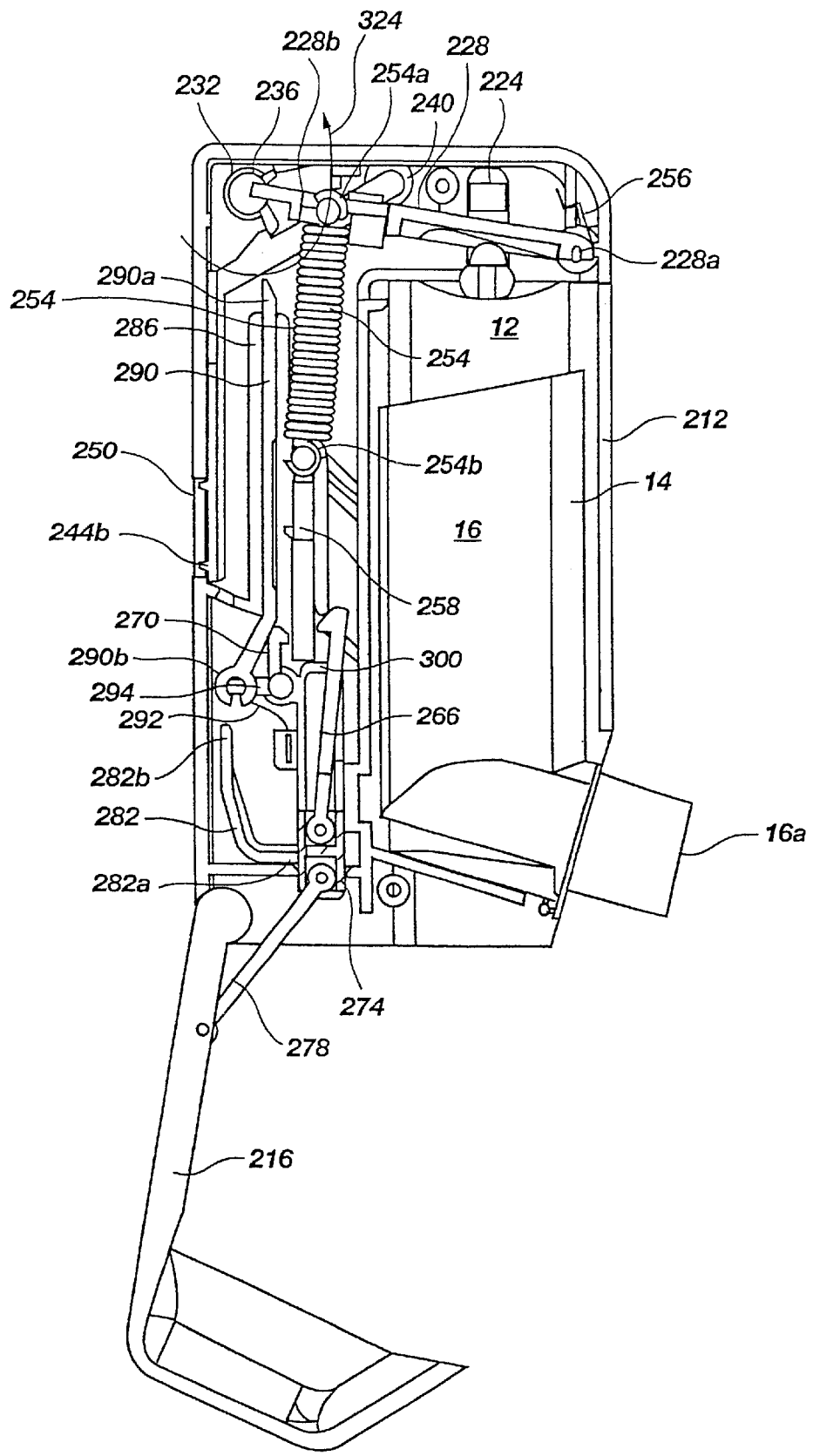
FIG. 3H shows a side view of the embodiment of FIGS. 3 through 3G at an end stage of the actuation cycle wherein the power spring has been returned to the position shown in FIG. 3 and wherein the canister of the metered dose inhaler is no longer in a vented position.

Removal of the latch 270 from the spring plate 258 leaves the lower end of the power spring 254 essentially unattached. The unattached power spring 254, in turn, no longer applies a downward pressure on the lever arm 228. Thus, as shown in FIG. 3H, the return spring 256 which is disposed adjacent the first end 228a of the lever arm 228 returns the lever arm to the first, upper position shown in FIG. 3. Movement of the lever arm 228 from the second position back into the first position lifts the plunger 224 from the aerosol canister 12 and allows the aerosol canister to return to the unvented position. Additionally, the compression spring which is integral to the metering chamber of the canister assists in returning the lever arm 228 to the first position as the compression spring in the cannister decompresses.

As the lever arm 228 returns to the upper position, the rotary sear 236 of the catch mechanism 232 rotates counterclockwise (as indicated by arrow 324 to again receive the distal end 228b of the lever arm. The rotary sear 236 will not rotate clockwise and release the lever arm 228 because the lever arm is biased into the upper position by the return spring 256. To overcome the biasing of the return spring 256, the power spring 254 must be in tension. Because the spring plate 258 is not being held by either the pawl 266 or the latch 270, no tension is present on the spring.

The latch 270 and the knock-off 290 are able to return to their normal positions due to a flat spring 292 connected to the knock-off and the lower part of the wall 300. The movement of the knock-off moves the rotatable arm 294 and the latch 270 to which it is attached. With the latch 270 rotated forwardly, the latch 270 is once again in position to secure the spring plate 258 when the spring plate is drawn down by the pawl 266.

As the user completes his or her inhalation, the internal vane spring 240 biases the internal vane 244 back into its initial position, wherein the lower end 244b is disposed immediately adjacent the rear air intake port 250. Rotation of the internal vane 244 places the tab 244c of the internal vane immediately adjacent with the tab 236a of the rotary sear 236. Thus, the catch mechanism 232 is again in place and configured to hold the lever arm 228 in the upper position until the internal vane 244 releases the catch mechanism and allows the power spring 254 to pull the lever arm downwardly.

FIGS. 3A through 3H have essentially shown the complete cycle of the device. By shutting the dust cap 216 shown in FIG. 3H, the device 200 is once again in a static state (like in FIG. 3A) wherein the internal vane spring 240, the power spring 254 and the return spring 256 are in non-load configurations.

Figure 4:
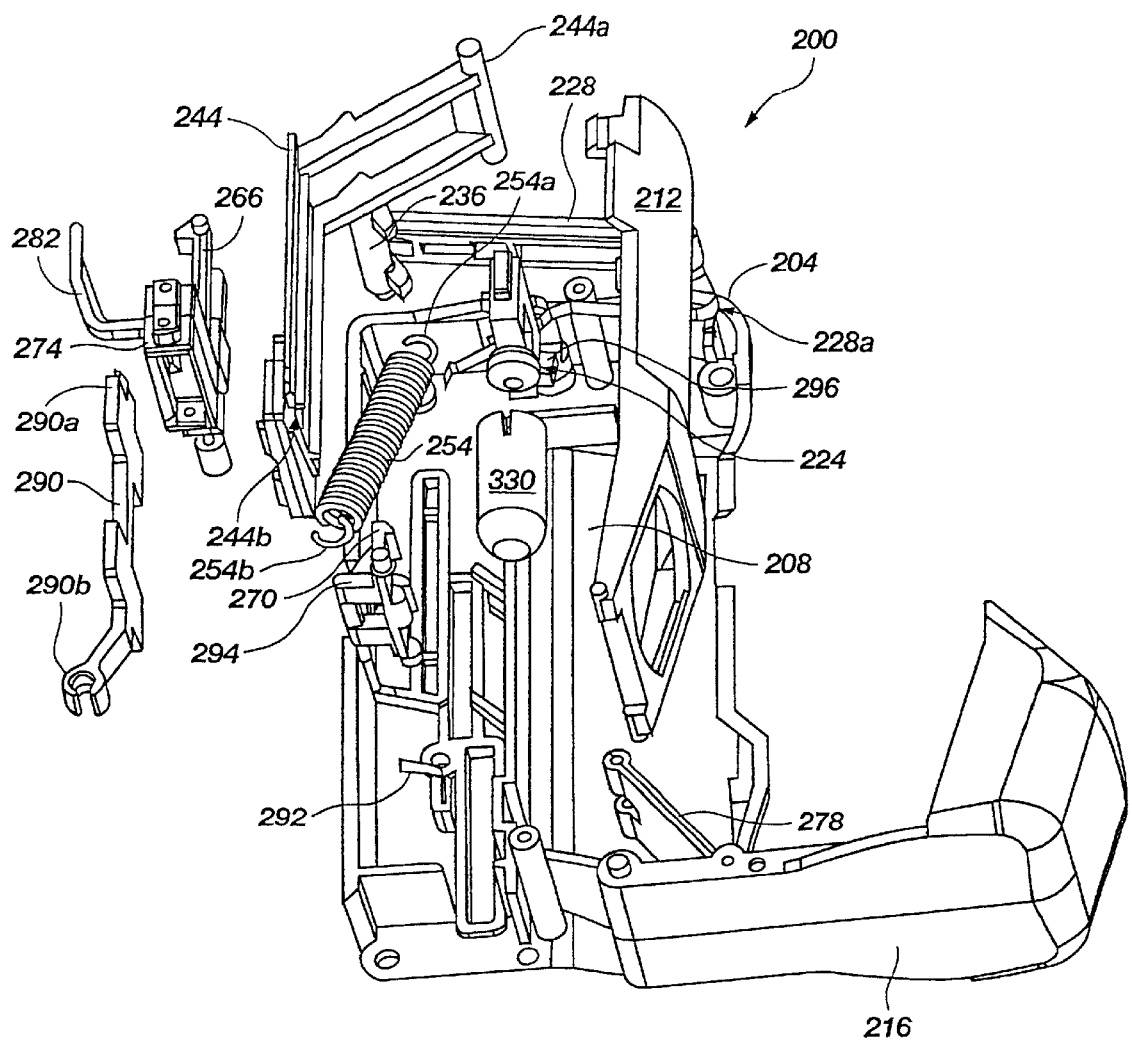
FIG. 4 shows an exploded view of the embodiment shown in FIGS. 3 through 3H to provide additional detail as to the structures of the actuator mechanism.

Turning now to FIG. 4, there is shown an exploded view of the device for use with metered dose inhalers, generally indicated at 200. The device 200 includes the body 204 configured to form a void 208 for receiving a metered dose inhaler (not shown). The metered dose inhaler is placed in the body through the door 212 disposed on the front side thereof.

To expose the metered dose inhaler, the dust cap 216 pivots with respect to the body 204. The dust cap is also attached to a connector arm which functions to arm the power spring 254 via the link block 274 and pawl 266. With the power 254 loaded, inhalation by the user of the device moves the internal vane 244 and thereby releases the lever 228 to move the plunger 224 downwardly to actuate the metered dose inhaler. Of course, an adapter 330 can be attached to the plunger 224 to facilitate use of the device 200 with metered dose inhalers which are smaller than the normal size. With the exception of the adapter, the device 200 functions the same way regardless of the height of the metered dose. inhaler.

After actuation of the metered dose inhaler, the knockoff 290 is moved to release the latch 270, thereby releasing the power spring 254 and allowing the lever 228 to be moved back into the initial position.

Figure 5:
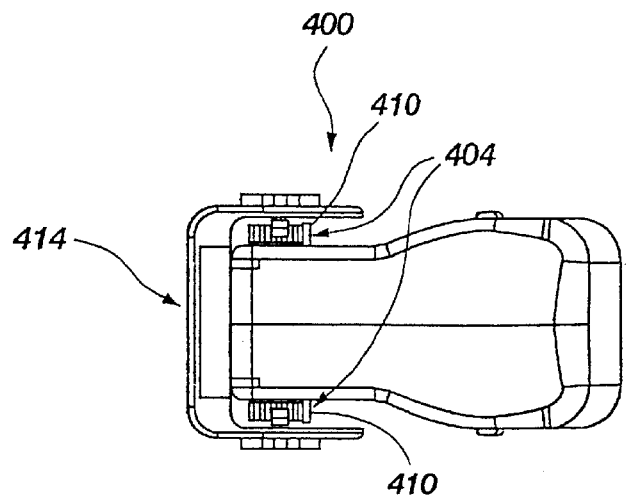
FIG. 5 shows a bottom view of a breath/inhalation actuated device with an alternate configuration for the damp block mechanism.

Turning now to FIG. 5, there is shown a bottom view of an alternate embodiment of a damping mechanism, similar in function to that shown previously at 296. Rather than attempting to slow the return of the lever 228 directly by being disposed on the lever 228, the damping mechanism, generally indicated at 400, is formed by a pair of spoked wheels 404 which are disposed on either side of the device.

An engagement rod 410 extends through the device and engages the spring plate 258 (FIGS. 3A through 3H). The ends of the engagement rod 410 engage the spoked wheels 404 of the. damping mechanism and thereby slows its upward movement. Slowing the upward movement of the engagement rod, in turn, slows the upward movement of the spring plate 258, thereby slowing the upward movement of the spring 254 and the lever arm 228. As with the other configuration of a damping mechanism, damp block 296, the purpose of such slowing to ensure that the aerosol canister has the appropriate amount of time to vent prior to the lever 228 returning to its original position.

The spoked wheels 404 which serve as the damping mechanism 400 are held in place by an external bracket 414.

Figure 5A:
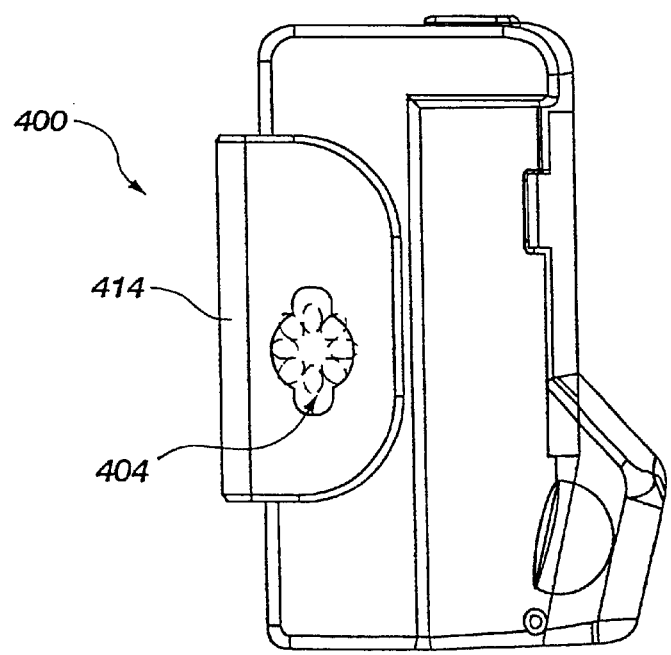
FIG. 5A shows a side view of the configuration of FIG. 5.

Turning now to FIG. 5A, there is shown a side view of a breath actuated device with the external bracket 414 disposed thereon. The position of one of the spoked wheels 404 forming the damping mechanism 400 are shown in shadow. In such a position, the damping mechanism provides minimal interference with the device, but functions well to appropriately slow the return movement of the lever 228.

Thus there is disclosed an improved inhalation actuated device for use with metered dose inhalers. Those skilled in the art will appreciate numerous modifications which can be made without departing from the scope and spirit of the, present invention. The appended claims are intended to cover such modifications.

What is claimed is:

1. A device for use with a metered dose inhaler including an actuator body and a medicament canister movable with respect to the actuator body to release medicament, the device comprising:

a body having a void formed therein configured for selectively holding the actuator body and medicament canister of a metered dose inhaler;

an actuator means disposed in the body adjacent the void for selectively moving the medicament canister with respect to the actuator body so as to actuate the metered dose inhaler when a metered dose inhaler is disposed in the void of the housing, the actuator means having an initial, unloaded position wherein the actuator means is in an unloaded state and a second, loaded position wherein the actuator means is in a loaded state, the actuator means comprising a lever arm and a plunger disposed in communication with the lever arm, the lever arm having an upper position wherein the lever arm holds the plunger in a first position wherein the plunger does not forcefully engage the medicament canister to release medicament in the metered dose inhaler and a lower position wherein the plunger is moved downwardly into a second position wherein the plunger engages the medicament canister of the metered dose inhaler and actuates the metered dose inhaler, and, the actuator means further comprising a biasing means for returning the lever arm to the upper position; and cocking means disposed in communication with the actuator means for placing the actuator means in the second loaded state wherein inhaling through the device releases the actuator means and actuates the metered dose inhaler.

2. The device according to claim 1, further comprising a first spring means for forcibly moving the lever arm from the upper position to the lower position.

3. The device according to claim 2, wherein the device further comprises release means for releasing the first spring means and thereby enabling the biasing means to return the lever arm to the upper position.

4. The device according to claim 1, further comprising a catch means disposed in communication with the lever arm for selectively holding the lever arm in the upper position.

5. The device according to claim 4, wherein the device further comprises a vane means movable by inhalation of the user, the vane means being disposed in communication with the catch means to selectively release the catch means, thereby allowing movement of the lever arm from the upper position to the lower position.

6. The device according to claim 1, wherein the device further comprises a cover means attached to the body and movable between a closed position and an open position, the cover means forming a portion of the cocking means.

7. A device for use with a metered dose inhaler including an actuator body and a medicament canister movable with respect to the actuator body to release medicament, the device comprising:

a body having a void formed therein configured for selectively holding the actuator body and medicament canister of a metered dose inhaler;

an actuator means disposed in the body adjacent the void for selectively moving the medicament canister with respect to the actuator body so as to actuate the metered dose inhaler when a metered dose inhaler is disposed in the void of the housing, the actuator means having an initial, unloaded position wherein the actuator means is in an unloaded state and a second, loaded position wherein the actuator means is in a loaded state, the actuator means comprising a lever arm and a plunger disposed in communication with the lever arm, the lever arm having an upper position wherein the lever arm holds the plunger in a first position wherein the plunger does not forcefully engage the medicament canister to release medicament in the metered dose inhaler and a lower position wherein the plunger is moved downwardly into a second position wherein the plunger engages the medicament canister of the metered dose inhaler and actuates the metered dose inhaler, and further comprising biasing means for returning the lever arm to the upper position; and cocking means disposed in communication with the actuator means for placing the actuator means in the second loaded state wherein inhaling through the device releases the actuator means and actuates the metered dose inhaler;

wherein the device further comprises a cover means attached to the body and movable between a closed position and an open position, the cover means forming a portion of the cocking means; and wherein the actuator means comprises spring means disposed in communication with the plunger for forcibly moving the plunger into the second position, the spring means having an unloaded orientation and a loaded orientation, and wherein movement of the cover means into the open position moves the spring means into the loaded position.

8. The device according to claim 7, wherein the spring means remains in the loaded orientation if the cover means is moved into the closed position without a user inhaling through the device.

9. The device according to claim 8, further comprising means for releasing the spring means from the loaded position after a user inhales through the device and the spring means moves the plunger from the first position to the second position.

10. An inhalation-actuated device for use with a metered dose inhaler formed by an actuator body and a medicament canister, the device comprising:

a housing having a void formed therein and configured for receiving the actuator body and medicament canister of the metered dose inhaler;

a cap means pivotable with respect to the body between a closed position and an open position for selectively exposing at least a portion of the actuator body when the metered dose inhaler is disposed within the body;

an actuator means disposed in the housing for selectively actuating the metered dose inhaler, the actuator means having a static, unloaded position and a loaded position, the actuator comprising a lever rotatable at one end for movement between an upper position wherein the actuator means does not forcefully engage a medicament canister of a metered dose inhaler when the metered dose inhaler is positioned in the housing, and a lower position, wherein the actuator means forcefully engages the medicament canister to actuate the metered does inhaler; and wherein the cap means is disposed in communication with the actuator means such that moving the cap means from the closed position to the open position moves the actuator means into the loaded position.

11. An inhalation-actuated device according to claim 10, wherein the actuator means comprises a power spring having a first, non-load position, and a second, loaded position, and wherein pivoting the cap means into the open position moves the power spring into the second, loaded position.

12. An inhalation-actuated device according to claim 11, wherein the actuator means further comprises a plunger, the plunger being disposed adjacent the void such that movement of the lever arm causes the plunger to actuate a metered dose inhaler disposed within the void.

13. An inhalation-actuated device according to claim 12, wherein the power spring is attached to the lever and provides a downward force sufficient to actuate a metered dose inhaler when the power spring is in the second, loaded position.

14. An inhalation-actuated device according to claim 13, wherein the actuator means further comprises a biasing means for biasing the lever-arm in the upper position.

15. An inhalation-actuated device according to claim 13, wherein the actuator means further comprises a catch means configured to selectively hold the lever arm in the upper position.

16. An inhalation-actuated device according to claim 15, wherein the actuator means further comprises a vane configured for movement by inhalation through the device, the vane being moveable between a first position wherein the vane holds the catch means and a second position wherein the vane releases the catch means to thereby enable the lever arm to move into the lower position.

17. An inhalation-actuated device according to claim 16, wherein the actuator means further comprises means for biasing the vane into the first position.

18. An inhalation-actuated device according to claim 13, wherein the power spring is held in the second position by a latch, and wherein movement of the lever into the second position releases the latch.

19. An inhalation-actuated device according to claim 18, further comprising a knock-off disposed functionally between the lever arm and the latch for moving the latch in response to downward movement by the lever arm.

20. An inhalation-actuated device according to claim 10, wherein the lever is configured for movement between a first, upper position and a second lower position, the lever causing actuation of a metered dose inhaler disposed in the void when in the second lower position and wherein the actuator means comprises:

a biasing means for encouraging the lever arm into the first, upper position;

a catch means configured for selectively holding the lever in the first, upper position;

a power spring for selectively applying a downward force on the lever to cause movement of the lever into the second, lower position when the catch means is not holding the lever arm in the first upper position, the power spring having a first, unloaded position wherein power spring does not provide sufficient downward force to move the lever from the first, upper position to the second, lower position, and a second loaded position wherein the power spring places sufficient downward force on the lever to move the lever into the second, lower position; and means for moving the power spring from the first, unloaded position to the second, loaded position.

21. An inhalation-actuated device for use with a metered dose inhaler formed by an actuator body and a medicament canister, the device comprising:

a housing having a void formed therein and configured for receiving the actuator body and medicament canister of the metered dose inhaler;

a cap means pivotable with respect to the body between a closed position and an open position for selectively exposing at least a portion of the actuator body when the metered dose inhaler is disposed within the body;

an actuator means disposed in the housing for selectively actuating the metered dose inhaler, the actuator means having a static, unloaded position and a loaded position, the actuator comprising a lever arm rotatable at one end for movement between an upper position wherein the actuator means does not forcefully engage a medicament canister of a metered dose inhaler when the metered dose inhaler is positioned in the housing, and a lower position, wherein the actuator means forcefully engages the medicament canister to actuate the metered does inhaler, and wherein the actuator means comprises a power spring having a first, non-load position, and a second, loaded position, and wherein pivoting the cap means into the open position moves the power spring into the second, loaded position;

wherein the cap means is disposed in communication with the actuator means such that moving the cap means from the closed position to the open position moves the actuator means into the loaded position; and wherein the power spring is attached to a spring plate, wherein the cap means is attached to a pawl, and wherein rotation of the cap means into the open position causes the pawl to engage the spring plate and pull the power spring into the second, loaded position.

22. An inhalation-actuated device for actuating a metered dose inhaler having a medicament canister and an actuator body, the inhalation-actuated device comprising:

a housing having a void configured for receiving the metered dose inhaler, such that the metered dose inhaler can be withdrawn from the housing;

an actuator assembly disposed in communication with said void for moving the medicament canister in the actuator body to thereby cause the release of medicament, the actuator having a first configuration wherein the actuator does not apply a movement force to the medicament canister and a second position wherein the actuator applies a movement force to the medicament canister to cause the release of medicament, the actuator comprising a lever rotatable between an upper position and a lower position, a plunger carried by the lever and configured to forcibly engage a medicament canister of a metered dose inhaler when a metered dose inhaler is disposed in the housing when the lever is in the lower position, but not when the lever is in the upper position, a first biasing element attached to the lever for forcefully drawing the lever from the upper position to the lower position, and a second biasing element engaging the lever for moving the lever from the lower position to the upper position.

* * * * *